United States Patent [19]

Morris et al.

[11] Patent Number: 4,909,919
[45] Date of Patent: Mar. 20, 1990

[54] VELOCITY MODULATED CAPILLARY ELECTROPHORESIS ANALYSIS SYSTEM

[75] Inventors: Michael D. Morris; Chang-Yuh Chen; Tshengedzeni Demana; Shi-Duo G. Huang, all of Ann Arbor, Mich.

[73] Assignee: The Regents of the University of Michigan, Ann Arbor, Mich.

[21] Appl. No.: 274,984

[22] Filed: Nov. 22, 1988

[51] Int. Cl.$^4$ .................. B01D 57/02; G01N 27/28
[52] U.S. Cl. ................. 204/299 R; 204/180.1; 204/183.3
[58] Field of Search ............. 204/299 R, 183.3, 180.1

[56] References Cited

PUBLICATIONS

Chen, C. Y. et al, "Capillary Zone Electrophoresis with Analyte Velocity Modulation, Application to Refractive Index Detection" Analytical Chemistry, 61(14) (1989), pp. 1590-1593.

*Primary Examiner*—John F. Niebling
*Assistant Examiner*—John S. Starsiak, Jr.
*Attorney, Agent, or Firm*—Harness, Dickey and Pierce

[57] ABSTRACT

A capillary zone electrophoresis system with analyte velocity modulation is described. Velocity modulation of the analyte is provided through applying an AC component to the DC driving potential applied to the separation capillary. Typically modulation on the order of 20 to 30% is applied by a separate AC power supply or an integral DC/AC source. Numerous types of detector systems can be employed including refractive index detectors, conductance, fluorescence, etc. The output of the detector is demodulated using a synchronous demodulation. The velocity modulation generates a signal which is a derivative of the conventional concentration/time signal. The system vastly improves detector sensitivity in situations where limitations are imposed by the large and variable background signals which arise from the aqueous buffer itself. Numerous embodiments of means for applying the modulated driving potential are described along with several detectors which can be implemented in systems according to this invention.

11 Claims, 4 Drawing Sheets

VELOCITY MODULATED CAPILLARY ELECTROPHORESIS ANALYSIS SYSTEM

This invention was made with government support under Contract No. GM37006 awarded by the Department Of Health And Human Services. The government has certain rights in the invention.

BACKGROUND OF THE INVENTION

This invention relates to capillary electrophoresis systems and particularly to such systems using analyte velocity modulation for improving detector sensitivity.

Capillary electrophoresis is a rapidly emerging high resolution separation technique, with broad applications in analytical chemistry, biochemistry adn molecular biology. It provides better resolution than liquid chromatography or one-dimensional gel electrophoresis. The capillary format is simpler to use than traditional slab gel elecrophoresis. Because it eliminates the delicate mechanical pump systems of liquid chromatography, an electrophoresis system is easier to maintain than liquid chromatographic instruments.

In free zone electrophoresis, the ionic analyte migrates in an electric field through a buffer-filled capillary. Separation is by ion mobility. The technique employs capillaries of 0.02-0.08 mm internal diameter. The capillaries are usually 500-1000 mm long. The operating voltage is typically 10,000-30,000 volts/meter. The driving voltage is provided by a hig voltage DC power supply. The analyte ions migrate along the capillary at slightly different rates and therefore reach the fixed detector at different times.

In a variant on the technique, the buffer contains micelles, which migrate through the capillary. Neutral analytes can partition between the moving micelles and the aqueous buffer. The neutrals, which all move by electro-osmosis at the same rate, are separated on the basis of their partition coefficients.

Gel-filled capillaries can be used to separate nucleic acids and denatured proteins. The gel filled capillaries are 0.2-0.3 mm diameter, and are 100-500 mm long. As with free zone electrophoresis, the operating voltages are 10,000-30,000 volts/meter. Typically, the gels and buffer systems of slab gel electrophoresis are used.

Capillary electrophoresis achieves hig resolution by use of high voltages and rapid migration rates. Ideally, the dominant zone-broadening (resolution limiting) effect is analyte diffusion. In practice, analyte adsorption on the capillary walls may also contribute. Much capillary electrophoresis research is devoted to techniques for eliminating or minimizing adsorption. At the usual migration times of 3-20 minutes, the zones migrate past the detector over a period of 2-10 seconds.

The capillaries must be narrow so that heat conduction is efficient and operating temperatures remain approximately constant. Rapid heat dissipation prevents convection, which would otherwise cause excessive zone broadening and loss of resolution. In free solution, it is known that convective effects are negligible if the capillary internal diameter is less than about 0.08 mm. The anti-convective effects of gels allows use of capillaries as wide as 0.3 mm internal diameter.

Absorbance detectors are the dominant detectors in capillary electrophoresis. They are used in many research applications and are employed in the one presently available commercial unit and in most or all of the commercial units currently under development. However, absorbance detectors are not as satisfactory as they have been in liquid chromatography. The narrow internal diameters of capillaries and small sample volumes employed are the source of insensitivity of absorbance detectors. The path length is short and the light throughput is small, so that such detectors are inadequately sensitive for many applications.

Fluorescence detectors are also known. Xenon flash lamps, arc lamps, mercury and zinc discharge lamps and He-Cd lasers have been used as excitation sources. Fluorescence is more sensitive than absorbance. However, most compounds of interest do not fluoresce, so a fluorescent derivative must be prepared before the separation or a post-capillary flow system must be used to prepare fluorescent derivatives of molecules as they exit the capillary. In either case, the basic simplicity of the capillary experiment is compromised.

Refractive index detectors have been described in the research literature. These devices are based on laser beam deflection. A laser beam, usually a He-Ne laser, is focused into the capillary. As the analyte passes through the beam, it causes the beam exiting the capillary to be deflected at a slightly different angle from the exit direction than when buffer only is present. These types of detectors are nearly universal in their application and can be implemented with a compact, inexpensive, low power laser, and an inexpensive beam position sensor. Such systems are especially applicable to protein and nucleic acid detection.

In another type of refractive index gradient detector, an extended laser beam or beam from a light emitting diode probes a length of capillary about 0.05-0.1 mm long. As the analyte zone passes through this region, its concentration gradient generates a refractive index gradient. This gradient causes the capillary to function as a prism of sorts. The exit angle of the beam is proportional to the refractive index or concentration gradient. This system probes a refractive index spatial gradient only. Accordingly, it does not suffer from some of the background drift problems of the conventional deflection detector, although drift due to beam pointing instability is still present.

Measurement of the change is conductance (inverse of electrical resistance) of the solution as the analyte passes by a pair of electrodes has been described. This technique is applicable to any ionic analyte whose conductance differs from that of the buffer. While the technique is nearly universal, it is difficult to implement because of the very small size of electrodes required.

Measurement of oxidation current with microelectrodes has also been reported. The technique gives very low detection limits, but the apparatus is delicate and difficult to fabricate. Mass spectrometry and Ruman spectrometry have been reported. These are special purpose and expensive techniques, which are indicated only when identification, rather than quantification is required.

Each of the detector systems described above are limited by fluctuations in the background signal from the buffer. The buffer is present at high concentration, typically about 0.01 M. The analyte may be present at concnentrations of 0.0001 M or less. The lower limit is whatever can be measured. The most important cause of background fluctuations is small (less than 1 degree Centigrade) fluctuations in the temperature of the capillary. The temperature dependence of the measured phenomenon results in a large drift in the background signal.

A secondary cause of background fluctuations is movement of the capillary, caused by changes in the electrical double layer at the surfaces of the capillary. The capillary adjusts its position in an attempt to maximize the separation between adjacent cationic and anionic charges on the surface. This movement slightly changes the efficiency of signal excitation and/or collection and changes the background.

Finally, drifts in the signal excitation source intensity or position or the detector response also cause changes in the background. In laser deflection detectors, laser beam pointing stability and beam intensity stability are both contributors.

Most of these sources of background fluctuation occur at relatively low frequencies, 0.001–10 Hz. Their effects can be eliminated by restricting the measurement to substantially higher frequencies. Fluctuations in excitation source intensity or detector response may occur at any frequency. They can be minimized by measurement in a narrow band of frequencies. These considerations show that a system in which the desired signal is modulated at a frequency above 10 Hz and demodulated in a narrow band system, such as by using a synchronous demodulator (lock-in amplifier) would yield a detector in which the effects of background drift are much smaller than in conventional systems. Moreover, many forms of modulation will generate a derivative response. A derivative system will prove especially advantageous in capillary electrophoresis. In this high resolution technique, bands are narrow and dC/dx is correspondingly large.

SUMMARY OF THE INVENTION

In view of the foregoing, devices in accordance with this invention employ systems for applying a driving voltage for capillary electrophoresis which is sinusoidally modulated (or pulsed), thereby modulating the zone velocity. Variations on this system include modulation with square waves or other symmetric waveforms, or pulse amplitude modulation. Detection is with a refractive index detector, conductivity detector, indirect fluorescence detector or any other detector which gives a response which is proportional to analyte concentration. The resulting modulated signal is demodulated with a synchronous demodulator, to yield a derivative signal which does not suffer from background drift. The modulation frequency is chosen to be above the range of thermal drifts and other slow fluctuations.

Recently, separation of nucleic acids on agarose gel slabs have employed brief and regular perturbations to the DC voltage in order to dislodge the molecules from the agarose gel and enhance resolution of the separated nucleic acids. The perturbations may be reversals of the field direction, pulses, or application of a second field at an angle to the driving field. The perturbations usually occur at low frequencies, typically below once per second. Detection is by evaluation of the gel after completion of the separation, using conventional stains or radioactive isotope techniques. Although the driving voltage might be said to be modulated, detection of the nucleic acid does not depend upon demodulation by means of a signal derived from the imposed pulses, field reversals or angled fields. These techniques are accordingly unrelated to this invention.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
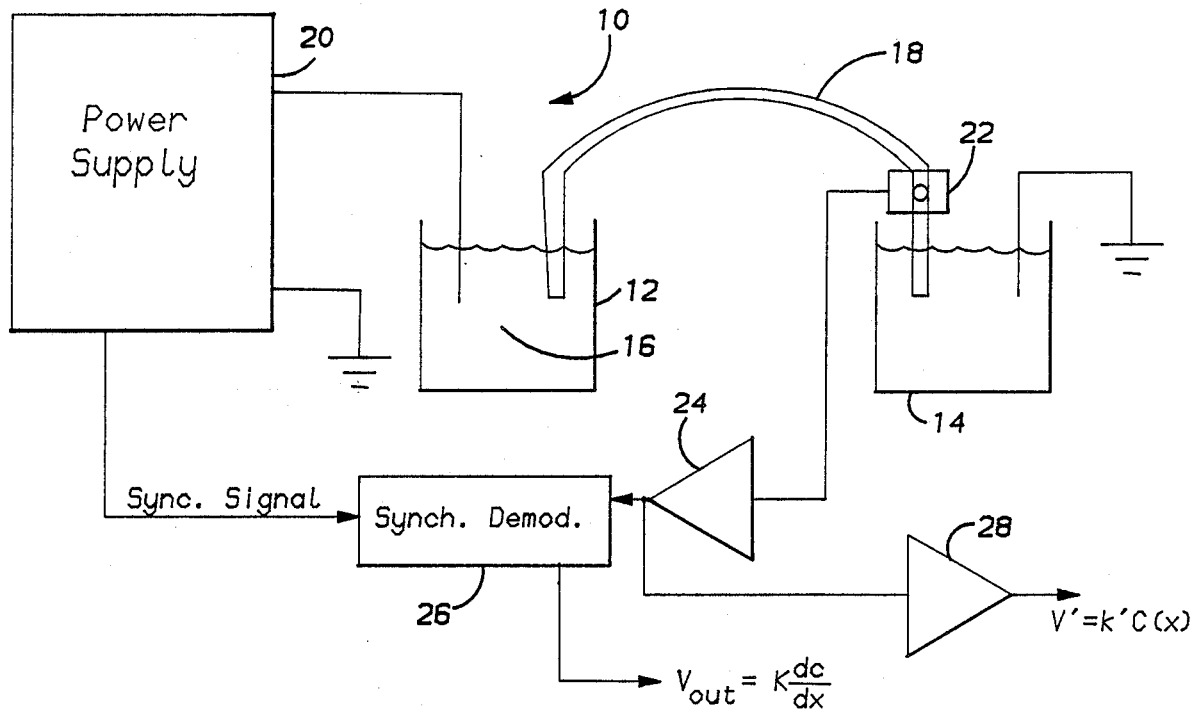
FIG. 1 is a schematic diagram of an electrophoresis analysis system according to a first embodiment of this invention using a power supply which produces an AC and DC output.

An electrophoresis analysis system in accordance with a first embodiment of this invention is shown in FIG. 1 and is generally designated by reference number 10. For this embodiment, a pair of separated buffer reservoirs 12 and 14 are provided which retain a buffer solution 16. Capillary tube 18 extends between the buffer reservoirs and also contains the buffer solution. A driving potential is applied by high voltage power supply 20 which provides an AC signal with a DC offset. The potential from power source 20 is applied to buffer reservoir 12, thus producing a potential difference across capillary 18 since buffer reservoir 14 is grounded. Detector 22 could be any one of numerous types such as described previously. The output signal from detector 22 is processed through amplifier 24. A reference synchronization signal related to the AC component of the output from power supply 20 is applied to synchronous demodulator 26.

Preferably, power supply 20 is designed to provide a constant high voltage DC output ($V_{DC}$) which would typically be in the range of 10,000 to 30,000 volts, and an alternating voltage ($V_{AC}$) which will typically have an amplitude of 25% to 100% of the DC voltage. The AC voltage may be derived from a reference oscillator or signal generator. The form of the AC voltage will generally be a sine wave or a square wave as the modulating waveform. In some cases, it may be convenient to use a train of regularly spaced modulating pulses.

At the exit of capillary 18, detector 22 senses the concentration of the analyte as it migrates past the detector region. Any existing or future detector technology can be used, provided that such detector responds to analyte concentration and that the measurement volume is small compared to the volume of the capillary occupied by the entire analyte sample. Alternatively, a detector which responds to concentration gradient can be employed to give a signal which will be the first derivative of the response obtained by a concentration detector.

A demodulation system is used to extract the modulated signal from the total detector response. If sine wave or square wave modulation is used, then any embodiment of a synchronous demodulator (also called lock-in detector or phase-sensitive detector) can be employed. If a pulse train is used, then any embodiment of a gated integrator can be employed.

The inventors have observed that sinusoidal or square wave modulation has no effect on the migration time of analytes or the DC response of the detector, as predicted by theory. The reason is that the average value of the AC modulation signal over one or more full cycles is identically zero. Increases in instantaneous migration velocity on one-half cycle are exactly balanced by decreases in instantaneous migration velocity on the other half-cycle. Overall, there is no difference in the migration behavior in this system as compared with conventional DC-only capillary electrophoresis system. Consequently, in any embodiment of this system, it is always possible to observe the DC detector response simultaneously with the modulated response, if desired. Such monitoring is obtained using low pass filter 28 which removes the AC modulation signal.

The inventors have observed that in pulsed operation, a pulse duty cycle of fraction 0.1 or less is desirable. Such pulses decrease the average analyte velocity by a fractional amount equal to the duty cycle fraction. Such velocity loss leads to an inversely proportional increase in migration time. This increase is however considered acceptable to achieve the benefits of pulsed voltage modulation.

As described previously, this invention is particularly useful in conjunction with detectors which generate a large background signal which originates from the buffer electrolyte in the capillary. Because such fluctuations are usually at frequencies below 10 Hz, it will be found convenient to modulate the driving potential at frequencies above 10 Hz. Because it is difficult and expensive to obtain high frequency response in high voltage amplifiers and modulators, and good high frequency compliance in high voltage DC power supplies, embodiments employing the system of FIG. 1 will most conveniently operate at modulation frequencies below about 200 Hz. It will be necessary to avoid modulation at the electric power distribution frequency and its harmonics or at frequencies at which any components of the system generate signals unrelated to the desired signal.

Figure 2:
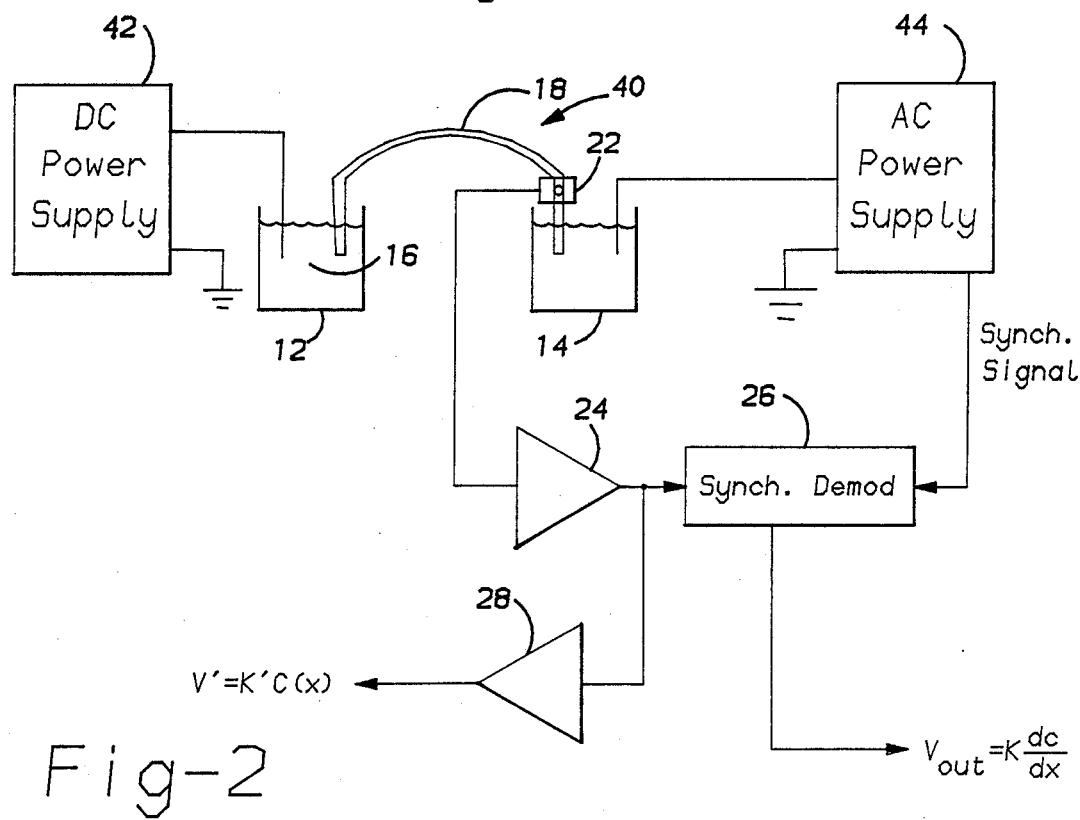
FIG. 2 is a schematic diagram of an electrophoresis analysis system according to a second embodiment of this invention utilizing separate sources for AC and DC voltage placed at opposite ends of the capillary.

Now with reference to FIG. 2, an electrophoresis analysis system according to a second embodiment of this invention is shown. Elements of this system and those described below which are identical to that of the first embodiment are identified by like reference numbers. In analysis system 40, generation of the DC and AC voltages take place in independent power supplies 42 and 44, respectively. Both these units are placed at opposite ends of capillary 18 in buffer reservoirs 12 and 14, and are referred to a common ground. The analyte velocity depends upon the voltage difference across the capillary tube 18 only, not upon the total voltage with respect to the system ground or other external reference points. The embodiment of FIG. 2 will be found particularly convenient because it allows the use of existing high voltage DC power supplies or for altering existing instruments which have been fitted with such supplies.

Figure 3:
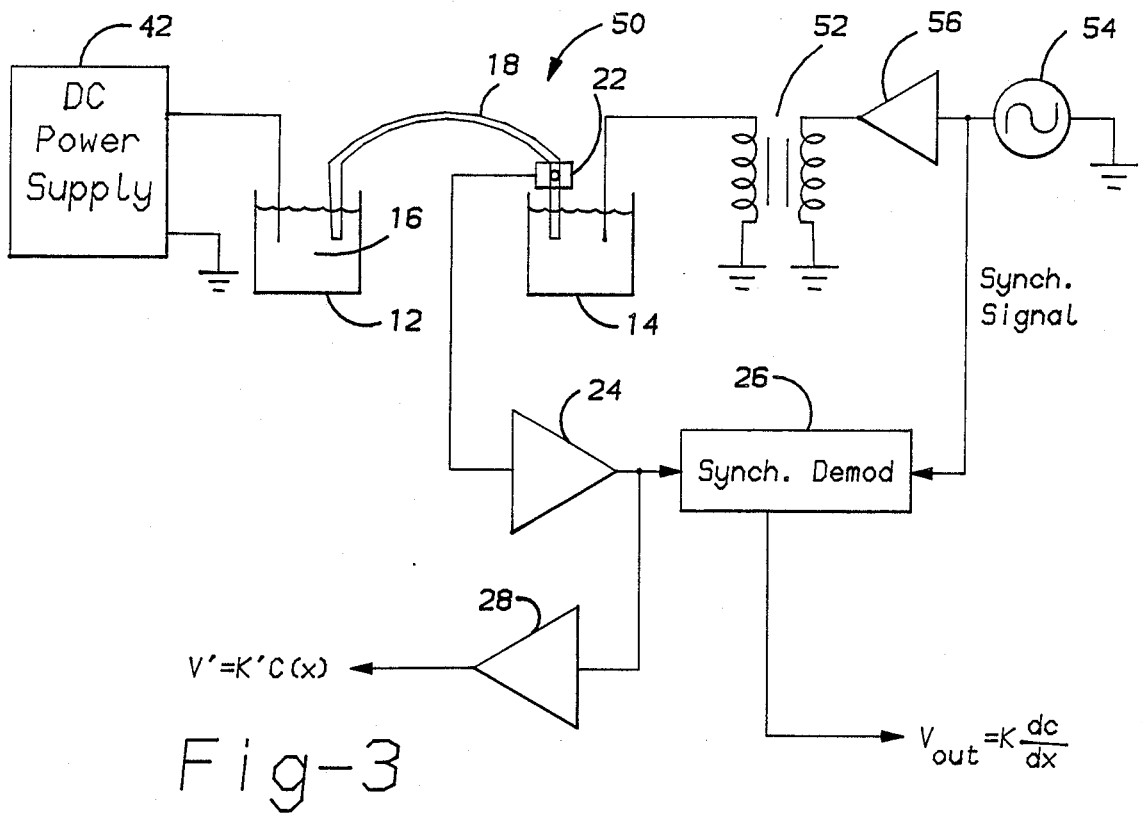
FIG. 3 is a schematic diagram of an electrophoresis analysis system according to a third embodiment of this invention where the AC and DC voltages are generated by independent sources placed at opposite ends of the capillary and wherein the AC source is provided by a step-up transformer and an oscillator/amplifier.

With respect to FIG. 3, a third embodiment of this invention is shown which is a specific design of the system shown in FIG. 2, and is generally designated by reference number 50. For this embodiment, DC power supply 42 is connected between buffer reservoir 12 and the system ground. The AC component of the signal is provided by step-up transformer 52 connected between buffer reservoir 14 and the system ground. The voltage signal to step-up transformer 52 is provided by oscillator 54 and amplifier Specially designed transformers may be employed for step-up transformer 52. In Amerian practice, such trnsformers are designed to be driven by 120 VAC/60 Hz signals and will function satisfactorily at 0–130 VAC drive voltages and over a frequency range of at least 20–500 Hz with sinuosidal or square wave modulation. Drive signals to such transformers may be provided by any convenient oscillator/amplifier combination. Oscillator 54 provides the reference signal to synchronous demodulator 26, which extracts the desired signal proportional to dC/dx from the total detector signal.

Figure 4:
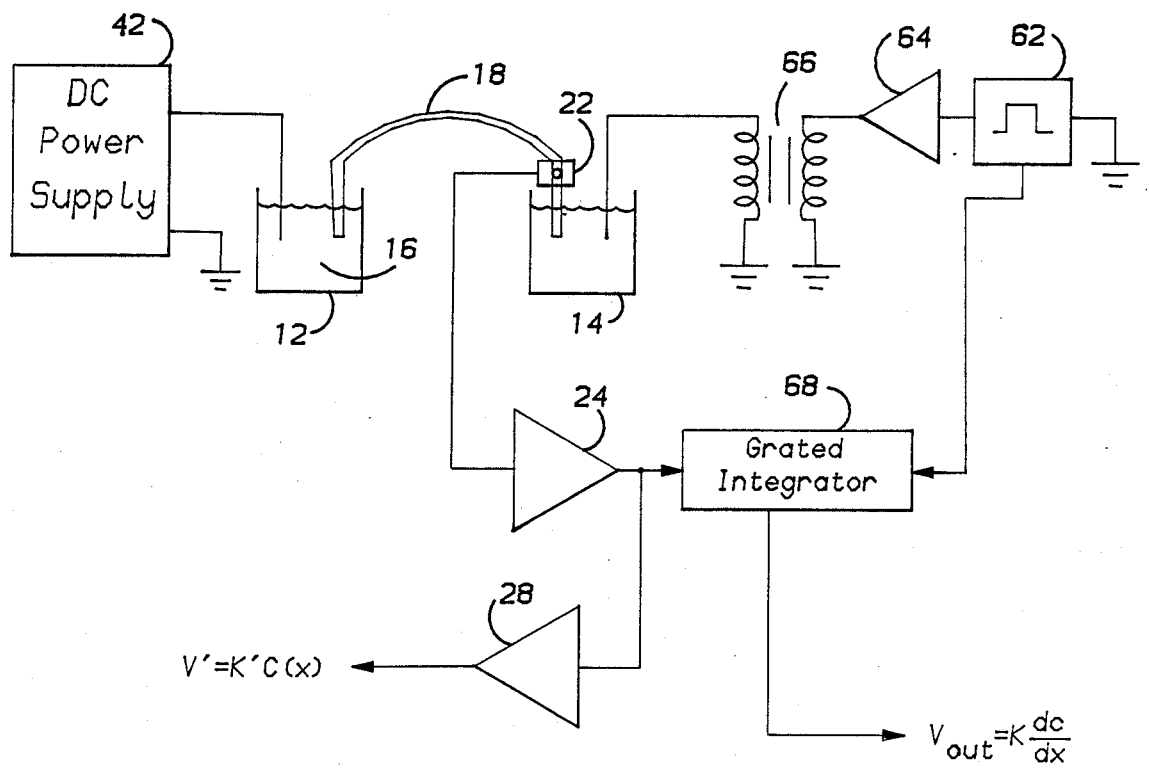
FIG. 4 is a schematic diagram of an electrophoresis analysis system according to a fourth embodiment of this invention in which the AC modulation signal is derived from a pulse generator/power amplifier combination and applied to a transformer designed for pulse operation.

FIG. 4 shows a fourth embodiment of this invention designated by reference number 60 in which the modulating signal is derived from pulse generator 62 and amplifier 64. This signal is applied to transformer 66 which is designed for pulse operation. A gated integrator 68 is used as a demodulator in place of demodulator 26 in accordance with the prior embodiments.

Figure 5:
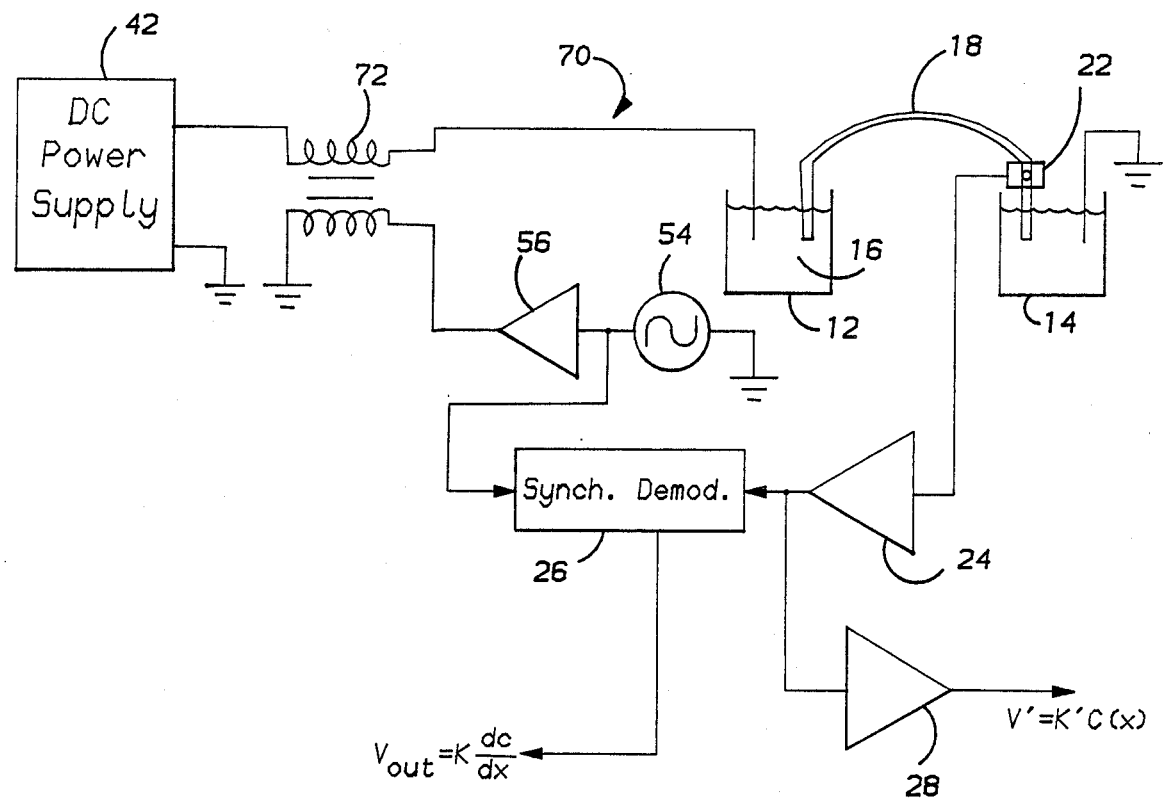
FIG. 5 is a schematic diagram of an electrophoresis analysis system according to a fifth embodiment in which the modulation voltage is provided by means of an oscillator/amplifier/step-up transformer.

FIG. 5 illustrates a fifth embodiment of this invention which is designated by reference number 70. In this embodiment, the modulation voltage is applied by means of oscillator 54, amplifier 56 and step-up transformer 72 as in FIG. 3. However, for this embodiment, the transformer output windings need not be grounded so that the DC power supply can remain at constant voltage and the transformer voltage changes. The voltage applied across capillary 18 is the instantaneous sum of the power supply and transformer voltages. The embodiment of FIG. 5 has the advantage of leaving the exit end of the capillary (reservoir 14) at the system ground. The system, however, has the disadvantage that transformer 72 must be capable of handling the high voltage applied DC potential.

Figure 6:
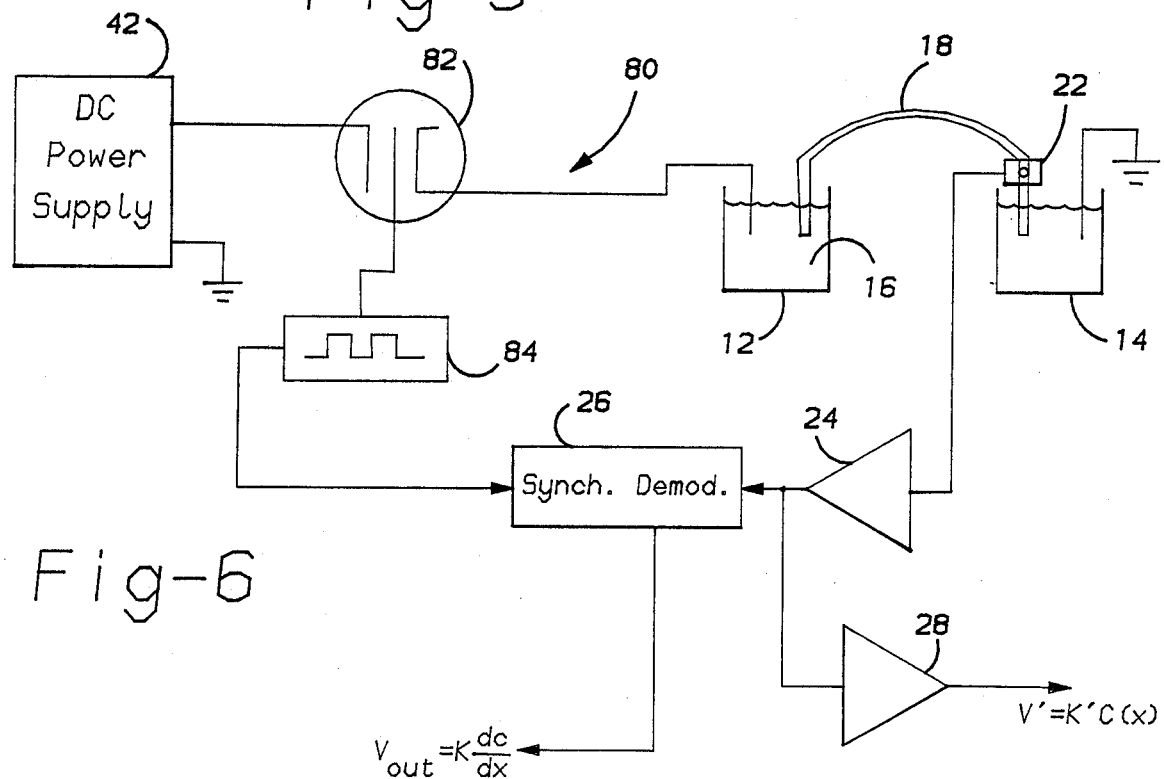
FIG. 6 is a schematic diagram of an electrophoresis analysis system in accordance with a sixth embodiment in which the modulation is provided by means of a high voltage amplifier.

The analysis system shown in FIG. 6 designated by reference number 80 also incorporates the features of FIG. 1 in that the modulation signal is provided by means of a high voltage amplifier rather than an independent power supply and transformers. The simplest embodiment of such an amplifier is a high voltage vacuum tube 82 or transistor amplifier operated as a switch to provide square wave or pulse modulation. Pulse generator 84 applies the modulation signal to tube 82 and a synchronization input to demodulator 26.

It is known to practitioners of capillary electrophoresis that the separation capillary usually maintains a nearly constant resistance. Consequently, it should be understood that modulation of the current flow through the capillary according to this invention will be equivalent to modulation of the voltage across it. Therefore, capillary electrophoresis systems in which circuitry designed explicitly to modulate current through the capillary rather than voltage across it are fully within the scope of this invention.

Figure 7:
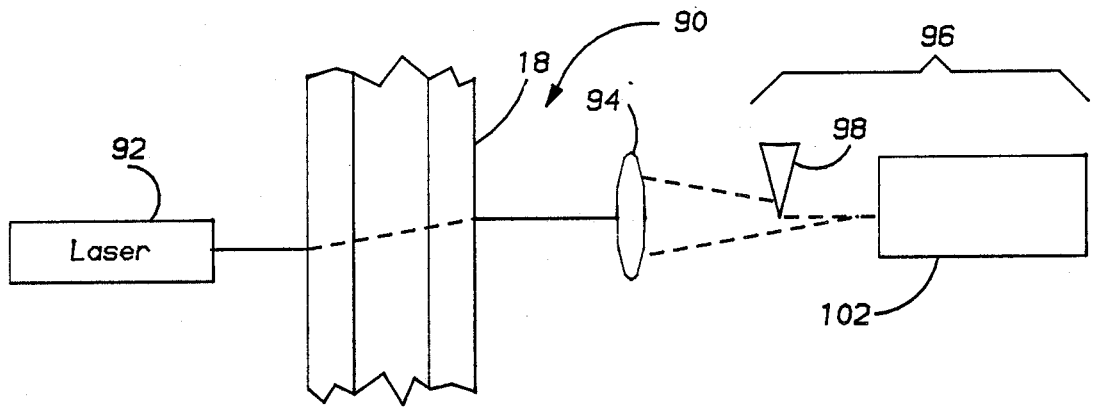
FIG. 7 is a schematic diagram of a refractive index detector which may be employed with electrophoresis analysis systems according to this invention.

FIG. 7 illustrates one embodiment of a refractive index detector 90 which may be used with any of the systems described above. The operating principle of the detector 90 is a measurement of the change in deflection of a light beam caused by the changing composition of the solution as analyte flows past the beam. Laser 92 is conveniently a diode laser having a power output of 1-10 mW. A laser whose output is visible is preferred, for convenience in adjustment of the system. At present, such visible lasers are commercially available with outputs at 750 nm. A diode laser is preferred over a gas (He-Ne) laser because the diode laser has intense fluctuations which are much smaller than those typically encountered in gas lasers. The beam emitted by laser 92 crosses capillary 18. Beyond the capillary 18, lens 94 (or a group of optical elements) is provided to recollimate or focus the beam onto position sensor 96 which is comprised of knife edge 98 and photodiode detector 102. This arrangement of position detector 96 enables the deflection of the beam passing through capillary 18 to be evaluated by differences in the degree of occlusion of the beam by knife edge 98. As an alternative to the above described configuration of position sensor 96, a split photodiode, a lateral effect photodiode or any other device which senses position of the beam from laser 92 can be employed.

Figure 8:
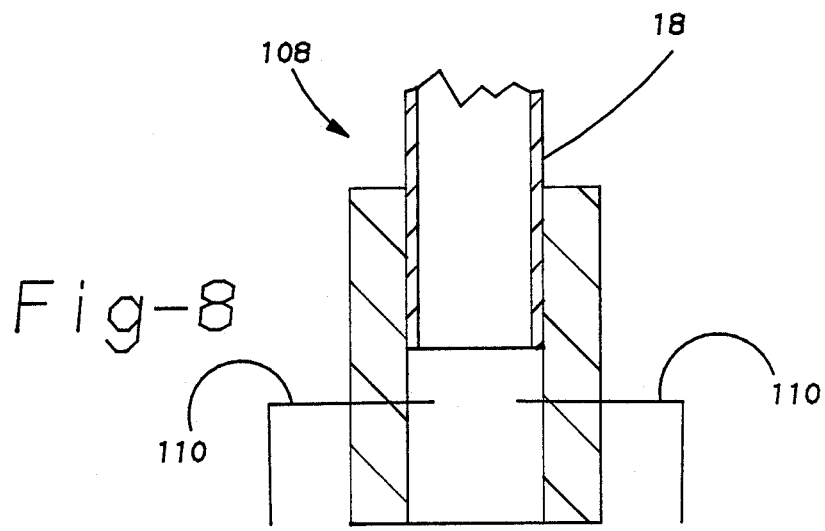
FIG. 8 is a partial schematic diagram of a conductance detector for use with electrophoresis analysis systems according to this invention.

FIG. 8 illustrates a conductance detector 108 for enabling analyte detection. Conductance detector 108 employs a pair of platinum or gold wires 110 which are conveniently no more than 0.0075 mm in diameter and are placed directly at the exit of capillary 18. Electroosmosis carries the analyte past the wires 110 and into buffer reservoir 16. The wires comprise one arm of a Wheatstone resistance bridge operating at a frequency which is conveniently 5,000-10,000 Hz, which will be much higher than the velocity modulation frequency. It will be found convenient to provide the bridge exciting voltage and to deliver the output by means of isolation transformers, opto-isolators or other systems designed to isolate small signals from high DC and AC voltages. The amplitude of the bridge unbalance signal contains a DC term which is proportional to the concentrations of buffer and analyte and a term at the velocity modulation frequency which is proportional to the rate of change of analyte concentration which is processed through a synchronous demodulator.

Figure 9:
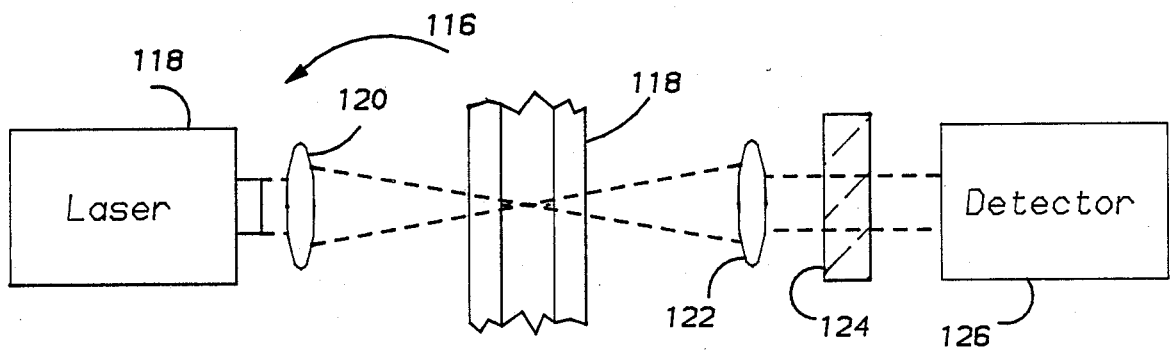
FIG. 9 is a schematic diagram of an indirect fluorescence detector for use with electrophoresis analysis systems according to this invention.

Now with reference to FIG. 9, an indirect fluroescence detector 116 is shown. For detector 116, laser 118 is provided whose beam is focused through lens 120 into capillary 18. The excited fluorescence emission is gathered by lens 122 and presented to filter 124 and photodiode detector 126 which responds to emission intensity. In regions containing the analyte, buffer ions are replaced by analyte ions so that the decrease in fluorescence is in direct proportion to the concentration of analyte. The output from photodiode 126 is demodulated to yield a signal proportional to the rate of change of concentration. A He-Cd laser operating at 325 nm or a zeon arc lamp and filters may be used to isolate ultraviolet emissions are at present the most practical fluorescence excitation sources. However, it should be understood that fluorescence derivatives could be specially prepared for blue, green or red light excitation enabling operation with an argon ion He-Ne or diode laser.

While the above description constitutes the preferred embodiments of the present invention, it will be appreciated that the invention is susceptible of modification, variation and change without departing from the proper scope and fair meaning of the accompanying claims.

We claim:

1. A capillary electrophoresis system comprising:
a capillary,
a buffer solution within said capillary,
power supply means for applying a driving potential across said capillary including a constant potential component and an alternating potential component such that an analyte within said capillary undergoes migration through said capillary at a velocity that is modulated by said alternating potential component,
detector means for sensing the presence of said analyte at a location along said capillary, and for providing an output signal which is related to the concentration of said analyte sensed by said detector means, and
demodulator means for receiving said detector output signal and receiving a syncrhonization signal related to said alternating potential component and for providing a demodulated output related to the concentration of said analyte at said detector.

2. A capillary electrophoresis system according to claim 1 further comprising a first and second buffer reservoir at each opposing end of said capillary and wherein said power supply means provides a difference of potential at said reservoirs to apply said potential difference across said capillary.

3. A capillary electrophoresis system according to claim 2 wherein said power supply means applies said driving potential to said first reservoir and said second reservoir is grounded.

4. A capillary electrophoresis system according to claim 2 wherein said power supply means comprises a constant potential source and a discrete alternating potential source.

5. A capillary electrophoresis system according to claim 4 wherein said constant potential source is applied to said first reservoir and said alternating potential source is applied to said second reservoir.

6. A capillary electrophoresis system according to claim 4 wherein both said constant potential and said alternating potential sources are applied to said first reservoir and said second reservoir is grounded.

7. A capillary electrophoresis system according to claim 4 wherein said alternating potential source comprises an oscillator, an amplifier, and a step-up transformer.

8. A capillary electrophoresis system according to claim 4 wherein said alternating potential source comprises a pulse generator, an amplifier, and a pulse transformer, and said demodulation means comprises a gated integrator.

9. A capillary electrophoresis system according to claim 1 wherein said detector means comprises a refractive index detector including a light source projecting a beam passing through said capillary and a photodetector for sensing the deviation of said beam through said capillary caused by refractice index deviations in said capillary caused by the presence of said analyte.

10. A capillary electrophoresis system according to claim 1 wherein said detector comprises a conductance detector including a pair of separated electrodes connected to signal processing means for evaluating the change in conductance between said electrodes caused by the presence of said analyte.

11. A capillary electrophoresis system according to claim 1 wherein said detector comprises a fluorescence detector comprising a light source for exciting fluorescence in said analyte within said capillary and a photodetector for evaluating said fluroescence.

* * * * *